(12) United States Patent
Centanni

(10) Patent No.: US 7,527,766 B2
(45) Date of Patent: May 5, 2009

(54) METHOD FOR DETERMINING THE EFFICIENCY OF A VAPORIZER IN A DECONTAMINATION SYSTEM

(75) Inventor: Michael A. Centanni, Parma, OH (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 11/971,242

(22) Filed: Jan. 9, 2008

(65) Prior Publication Data

US 2008/0110240 A1     May 15, 2008

Related U.S. Application Data

(62) Division of application No. 10/844,468, filed on May 12, 2004.

(51) Int. Cl.
*G01N 33/00* (2006.01)

(52) U.S. Cl. .................................................. 422/68.1

(58) Field of Classification Search ................. 422/68.1
See application file for complete search history.

(56) References Cited

U.S. PATENT DOCUMENTS

| | | | | |
|---|---|---|---|---|
| 3,164,004 A | 1/1965 | King, Jr. | ................... | 73/24.06 |
| 3,327,519 A | 6/1967 | Crawford | ................... | 73/24.06 |
| 3,464,797 A | 9/1969 | Hagopain | | |
| 3,636,444 A | 1/1972 | Strawn et al. | .................. | 324/61 |
| 3,778,706 A * | 12/1973 | Thompson | ................. | 324/668 |
| 4,163,384 A | 8/1979 | Blakemore | ..................... | 73/29 |
| 4,219,776 A | 8/1980 | Arulanandan | ................ | 324/323 |
| 4,236,893 A | 12/1980 | Rice | ......................... | 23/230 B |
| 4,242,096 A | 12/1980 | Oliveira et al. | ............ | 23/230 B |
| 4,314,821 A | 2/1982 | Rice | ......................... | 23/230 B |
| 4,427,772 A | 1/1984 | Kodera et al. | ................. | 435/27 |
| 4,525,265 A | 6/1985 | Abe et al. | ................... | 204/403 |
| 4,674,879 A | 6/1987 | Gregorig et al. | ............ | 356/301 |
| 4,788,466 A | 11/1988 | Paul et al. | ................... | 310/316 |
| 4,849,178 A | 7/1989 | Azuma | ........................ | 422/69 |
| 4,857,152 A | 8/1989 | Armstrong et al. | .......... | 204/1 T |
| 5,157,968 A | 10/1992 | Zfira | ........................... | 73/149 |
| 5,243,858 A | 9/1993 | Erskine et al. | ........... | 73/204.26 |
| 5,339,675 A | 8/1994 | DiLeo et al. | ................ | 73/24.04 |

(Continued)

FOREIGN PATENT DOCUMENTS

WO     WO 98/57673     12/1998

OTHER PUBLICATIONS

U.S. Appl. No. 10/456,378, filed Jun. 6, 2003, Centanni, entitled: Method and Apparatus for Formulating and Controlling Chemical Concentrations in a Solution.

(Continued)

*Primary Examiner*—Walter D Griffin
*Assistant Examiner*—Bobby Ramdhanie
(74) *Attorney, Agent, or Firm*—Kusner & Jaffe; Michael A. Centanni

(57) ABSTRACT

An apparatus for determining the efficiency of a vaporizer in a decontamination system, having a first sensor for generating a first signal indicative of the concentration of a decontaminating chemical in a liquid decontaminate before vaporization by a vaporizer, and a second sensor for generating a second signal indicative of the concentration of vaporized decontaminate after vaporization by said vaporizer, and means for determining efficiency in accordance with said first and second signal.

11 Claims, 5 Drawing Sheets

U.S. PATENT DOCUMENTS

| | | | | |
|---|---|---|---|---|
| 5,364,510 | A | 11/1994 | Carpio | 204/153.1 |
| 5,439,569 | A | 8/1995 | Carpio | 204/153.1 |
| 5,459,568 | A | 10/1995 | Yano et al. | 356/336 |
| 5,470,754 | A | 11/1995 | Rounbehler et al. | 436/106 |
| 5,595,908 | A | 1/1997 | Fawcett et al. | 435/287.2 |
| 5,600,142 | A | 2/1997 | Van Den Berg et al. | 250/339.13 |
| 5,630,878 | A | 5/1997 | Miyamoto et al. | 118/715 |
| 5,700,375 | A | 12/1997 | Hagen et al. | 210/651 |
| 5,756,631 | A | 5/1998 | Grate | 528/26 |
| 5,847,276 | A | 12/1998 | Mimken et al. | 73/453 |
| 5,856,198 | A | 1/1999 | Joffe et al. | 436/100 |
| 5,866,798 | A | 2/1999 | Schönfeld et al. | 73/24.06 |
| 5,882,590 | A * | 3/1999 | Stewart et al. | 422/28 |
| 5,958,787 | A | 9/1999 | Schönfeld et al. | 436/116 |
| 6,171,867 | B1 | 1/2001 | Feucht et al. | 436/124 |
| 6,196,052 | B1 | 3/2001 | May et al. | 73/24.06 |
| 6,369,387 | B1 | 4/2002 | Eckles | 250/343 |
| 6,410,332 | B1 | 6/2002 | Desrosiers et al. | 436/37 |
| 6,454,874 | B1 | 9/2002 | Jacobs et al. | 134/18 |
| 6,560,551 | B1 | 5/2003 | Severson et al. | 702/54 |
| 6,614,242 | B2 | 9/2003 | Matter et al. | 324/698 |
| 6,630,560 | B2 | 10/2003 | McGill et al. | 528/25 |
| 7,232,545 | B2 * | 6/2007 | Centanni et al. | 422/3 |
| 2003/0063997 | A1 | 4/2003 | Fryer et al. | 422/3 |
| 2003/0112431 | A1 | 6/2003 | Ketkar | 356/316 |
| 2005/0013726 | A1 | 1/2005 | Hill et al. | 422/3 |

OTHER PUBLICATIONS

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/667,988, filed Sep. 22, 2003, Korenev et al., entitled: Method and Apparatus for Measuring the Concentration of Hydrogen Peroxide in a Fluid.

T. J. Buckley et al., "*Toroidal Cross Capacitor for Measuring the Dielectric Constant of Gases*," Review of Scientific Instruments, vol. 71, No. 7, Jul. 2000, pp. 2914-2921.

Gross et al., "*The Dielectric Constants of Water Hydrogen Peroxide and Hydrogen Peroxide-Water Mixtures*," L. Amer. Chem. Soc., vol. 72, 1950, pp. 2075-2080.

"*Humidity Sensor Theory and Behavior*," Psychometrics and Moisture, Honeywell HVAC, Nov. 27, 2002.

Philipp, "*Charge Transfer Sensing*," 1997.

Wojslaw, "*Everything You Wanted to Know About Digitally Programmable Potentiometers*," Catalyst Semiconductor, Inc., Oct. 17, 2001, Publication No. 6009.

Kittel, "*Introduction to Solid State Physics*," Fourth Edition, John Wiley & Sons, Inc., 1971.

Philipp, "*The Charge Transfer Sensor*," Sensors Magazine, Oct. 1999.

Steven J. Lasky, Howard R. Meyer & Daniel A. Buttry, Department of Chemistry, "Quartz Microbalance Studies of Solvent and Ion Transport in Thin Polymer Films in Sensor Applications of the QCH," *Technical Digest* 1990, pp. 1-4.

Sylvain Lazare and Vincent Granier, "Excimer Laser Light Induced Ablation and Reactions at Polymer Surfaces as Measured with a Quartz-Crystal Microbalance," Nov. 16, 1987, J. Appl. Phys 63 (6), Mar. 15, 1988, 1988 *American Institute of Physics*, pp. 2110-2115.

Stanley Bruckenstein, C. Paul Wilde, Michael Shay and A. Robert Hillman, "Experimental Observations on Transport Phenomena Accompanying Redox Switching in Polythionine Films Immersed in Strong Acid Solutions," 1990 American Chemical Society, pp. 787-793.

Robert R. McCaffrey, Stanley Bruckenstein and Paras N. Prasad, "Novel Application of the Quartz Crystal Microbalance to Study Langmuir-Blodgett Films," 1986 *American Chemical Society*, pp. 228-229.

J.A. Moore and Sang Youl Kim, "Diffusion of Small Molecules in Radiation Damaged PMMA Thin Films," 2002 Engineering Info. Inc., pp. 383-386.

Rade Ognjanovic, C.-Y. Hui, E.J. Kramer, "The Study of Polystyrene Surface Swelling Microbalance and Rutherford Backscattering Techniques," *Journal of Materials Science* 25 (1990), 1990 Chapman and Hall Ltd., pp. 514-518.

H.G. Tompkins, "Use of Surface and Thin Film Analysis Techniques to Study Metal-Organic and Metal-Polymer Interaction: A Review," *Thin Solid Films*, 119 (1984), pp. 337-348.

Sylvain Lazare, Jean Claude Soulignac and Pascal Fragnaud, "Direct and Accurate Measurement of Etch Rate of Polymer Films under Far-UV Irradiation," Appl. Phys. Lett. 50 (10), Mar. 9, 1987, 1987 American Institute of Physics, pp. 624-625.

Aljosa Vrhunec, Andreja Kolenc, Dusan Teslic, Iztok Livk and Ciril Pohar, "Crystal Size Distribution in Batch Sodium Perborate Precipitation,"*Acta Chim. Slov.* 1999, 46(4), pp. 543-554.

* cited by examiner

METHOD FOR DETERMINING THE EFFICIENCY OF A VAPORIZER IN A DECONTAMINATION SYSTEM

RELATED APPLICATIONS

This application is a divisional of U.S. application Ser. No. 10/844,468, filed May 12, 2004.

FIELD OF THE INVENTION

The present invention relates generally to a decontamination process, and more particularly to a method and apparatus for determining the efficiency of a vaporization system for a decontamination system.

BACKGROUND OF THE INVENTION

Vaporization systems are used in decontamination systems to produce gases such as vaporized hydrogen peroxide. As used herein, the term "decontamination" refers to processes, including, but not limited to, "deactivation of biocontamination," "deactivation of chemical contamination," "sterilization," "disinfection" and "sanitization." In the case of a typical hydrogen peroxide decontamination system, an aqueous solution of hydrogen peroxide is delivered to a vaporizer where the aqueous solution of hydrogen peroxide is vaporized. The resulting mixture of vaporized hydrogen peroxide and water vapor is then injected into a treatment chamber, where articles are decontaminated by exposure to the vaporized hydrogen peroxide.

Efficient vaporization of the aqueous solution of hydrogen peroxide is important to the effective operation of a decontamination system using vaporized hydrogen peroxide. The aqueous solution of hydrogen peroxide is typically comprised of liquid hydrogen peroxide diluted with water. When solutions are vaporized, a disproportionate amount of the more volatile component will vaporize first. In the case of the abovementioned aqueous solution of hydrogen peroxide, water is more volatile than hydrogen peroxide and therefore vaporizes more quickly than the liquid hydrogen peroxide. Thus, the water vapor reaches the articles in the treatment chamber to be decontaminated before the hydrogen peroxide vapor, and in higher concentrations. Consequently, the water vapor becomes an effective barrier to hydrogen peroxide penetration around small crevices and lumens of the articles in the treatment chamber.

In view of the aforementioned problem, decontamination systems have been developed that vaporize an aqueous solution of hydrogen peroxide by injecting the aqueous solution of hydrogen peroxide into a vaporization chamber, wherein successive increments of the aqueous solution of hydrogen peroxide are metered onto a heated surface inside the vaporization chamber. Each increment of the aqueous solution of hydrogen peroxide is substantially instantaneously vaporized before the next succeeding increment of the aqueous solution hydrogen peroxide is metered onto the heated surface.

One problem with such systems is that over time the concentration of vaporized hydrogen peroxide within the system may not reach desired levels because the efficiency level of the vaporizer may have decreased. Efficient vaporization of an aqueous solution of hydrogen peroxide depends upon substantially instantaneous vaporization of an increment of the aqueous solution of hydrogen peroxide. When an increment of the aqueous solution of hydrogen peroxide does not substantially instantaneously vaporize, the efficiency of the vaporizer decreases. Such a decrease in efficiency may occur because deposits develop on surfaces that contact and transmit heat to the aqueous solution of hydrogen peroxide. The decreased efficiency will result in lower than desired concentrations of vaporized hydrogen peroxide within the decontamination system. A reduction in the concentration of vaporized hydrogen peroxide within the system may result in reduced efficacy of decontamination or increased decontamination times.

The present invention provides an apparatus and a method for determining the efficiency of a vaporizer in a decontamination system.

SUMMARY OF THE INVENTION

In accordance with a preferred embodiment of the present invention, there is provided an apparatus for determining the efficiency of a vaporizer in a decontamination system, comprising: (a) a first sensor for generating a first signal indicative of the concentration of a decontaminating chemical in a liquid decontaminate before vaporization by a vaporizer; (b) a second sensor for generating a second signal indicative of the concentration of vaporized decontaminate after vaporization of the liquid decontaminate by said vaporizer; and (c) means for determining efficiency in accordance with said first and second signals.

In accordance with another aspect of the invention, there is provided a method for determining efficiency of a vaporizer for a vaporization process, the method comprising the steps of: (a) exposing a liquid decontaminate including a decontaminating chemical to a first sensor to determine the concentration of the decontaminating chemical in the liquid decontaminate; (b) vaporizing the liquid to produce a gas including a vaporized decontaminate; and (c) exposing the gas to a second sensor to determine the concentration of the vaporized decontaminate.

In accordance with yet another aspect of the present invention, there is provided a method for determining a vaporization efficiency of a vaporizer in a decontamination system, the method comprising the steps of: (a) exposing a first sensor to a liquid, said liquid being comprised of a decontaminating chemical and at least one other component, wherein said liquid is supplied to a vaporizer; (b) vaporizing said liquid in said vaporizer to generate a gas; (c) exposing a second sensor to said gas, said gas being comprised of a vaporized decontaminate and at least one other component; (d) determining a concentration of decontaminating chemical in said liquid; and (e) determining a concentration of decontaminate in said gas.

An advantage of the present invention is the provision of a method and apparatus for determining the efficiency of vaporization for a vaporizer used in connection with a decontamination system.

Another advantage of the present invention is the provision of a method and apparatus for comparing the efficiency of vaporization to a base line efficiency of vaporization.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
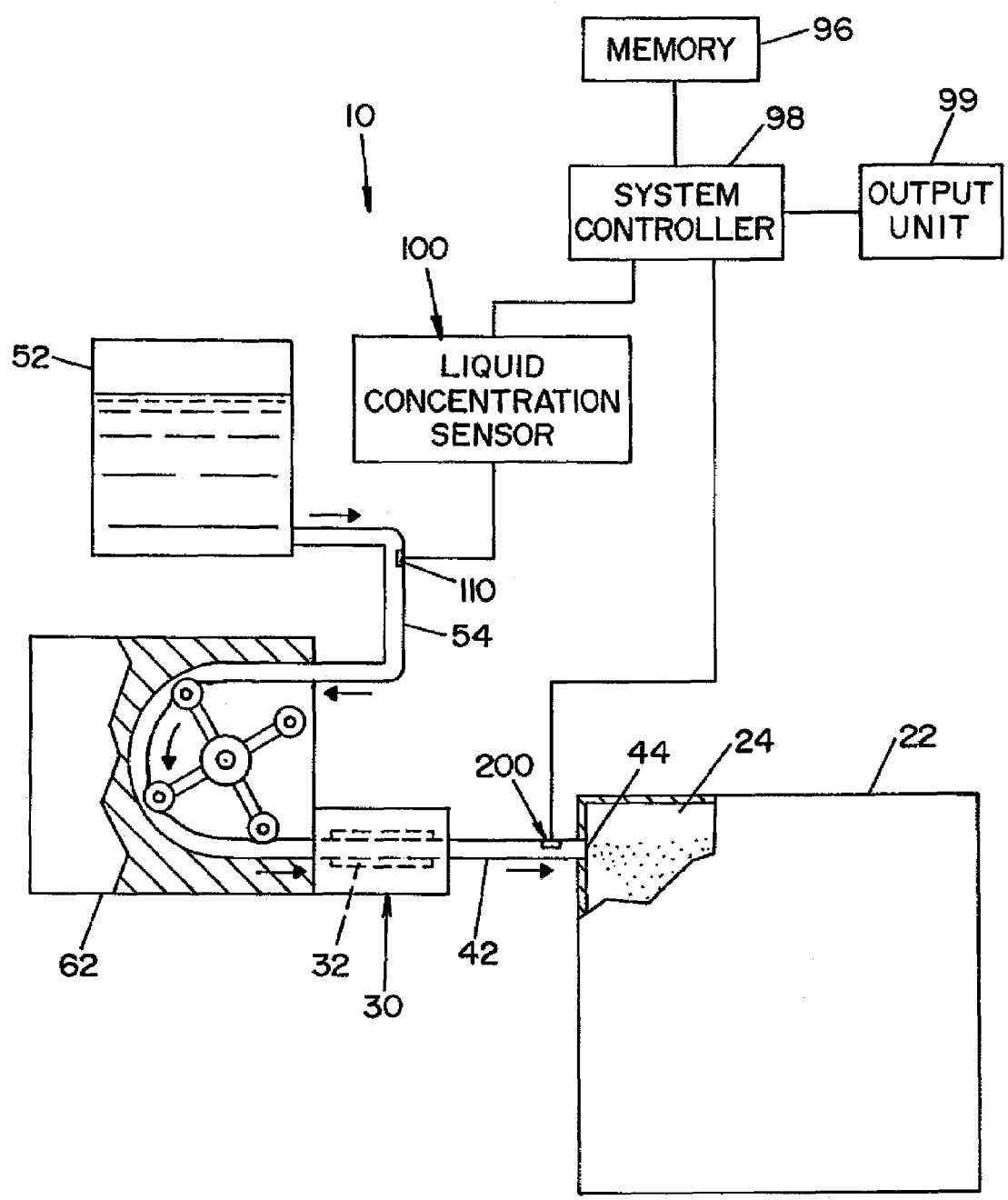
FIG. 1 is a schematic view of an exemplary vaporized hydrogen peroxide decontamination system including an apparatus for determining the efficiency of vaporization according to a preferred embodiment of the present invention.

Referring now to the drawings wherein the showings are for the purpose of illustrating the invention only, and not for the purpose of limiting same, FIG. 1 shows an exemplary decontamination system 10. Decontamination system 10 is generally comprised of a liquid decontaminate supply 52, a pump 62, a vaporizer 30, a room or housing 22 that defines a region or treatment chamber 24, a system controller 98, a liquid concentration sensor 100, and a vapor concentration sensor 200. Decontamination system 10 is an "open loop" system. It should be understood that the present invention is also suitably used in connection with a "closed loop" system.

In the embodiment shown, liquid decontaminate supply 52 provides a liquid decontaminate through feed line 54 to pump 62. It is recognized that the liquid decontaminate may be comprised of one or more liquid decontaminating chemicals, or one or more liquid decontaminating chemicals in combination with one or more chemicals that are not decontaminating chemicals. In the illustrated embodiment, the liquid decontaminate provided by liquid decontaminate supply 52 is an aqueous solution of hydrogen peroxide. Pump 62 is driven by a motor (not shown) and is provided to convey metered amounts of the liquid decontaminate to vaporizer 30 from liquid decontaminate supply 52.

Vaporizer 30 is a vaporizer as is conventionally known for the vaporization of liquid decontaminates. Vaporizer 30 vaporizes the liquid decontaminate using a conventionally known heating element 32. Heating element 32 has evaporation surfaces operable to vaporize metered amounts of liquid decontaminate. The vaporized components of the liquid decontaminate exit vaporizer 30 through supply conduit 42, and enter treatment chamber 24 through inlet port 44.

In a preferred embodiment, system controller 98 is a microprocessor, microcontroller, processor, processing unit, or like device programmed to control the operation of system 10. As illustrated in FIG. 1, system controller 98 is connected to an output unit 99 and a memory 96. Output unit 99 provides information to the operator in an audible and/or visual form. Accordingly, output unit 99 may take the form of an audio speaker and/or a visual display unit. Memory 96 provides data storage capabilities for system controller 98. Additionally, system controller 98 is electrically connected to liquid concentration sensor 100 and vapor concentration sensor 200.

In the illustrated embodiment, system 10 is a decontamination system for decontaminating objects with hydrogen peroxide, and more particularly, with vaporized hydrogen peroxide. Accordingly, liquid concentration sensor 100 and vapor concentration sensor 200 shall be described with respect to determining the concentration of hydrogen peroxide in an aqueous solution, and as a part of a two-component, vapor-phase mixture where water vapor is a second component.

In the illustrated embodiment, liquid concentration sensor 100 is of the type described in U.S. application Ser. No. 10/389,036, filed Mar. 14, 2003, entitled "Method and Apparatus for Measuring Chemical Concentration in a Fluid," which is fully incorporated herein by reference, and described further below.

Figure 2:
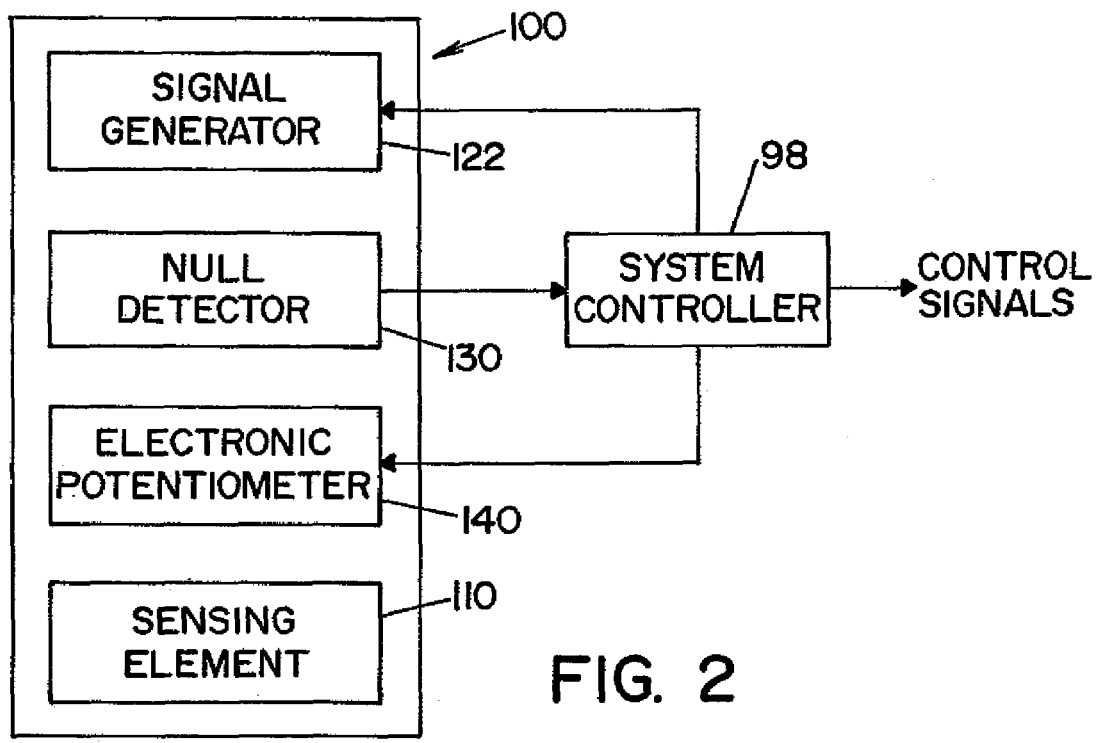
FIG. 2 is a block diagram of an exemplary sensor for determining the concentration of a liquid chemical, according to a first embodiment.
Figure 3:
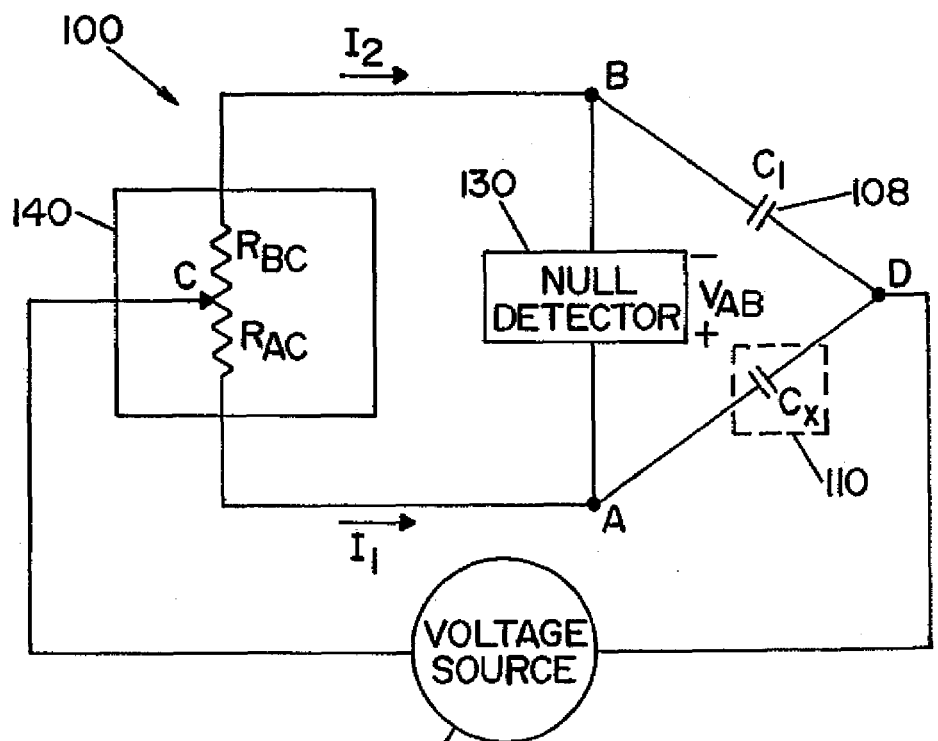
FIG. 3 is a schematic diagram of the sensor system of FIG. 2.

Referring now to FIG. 2, there is shown a block diagram of an exemplary liquid concentration sensor 100 according to a first embodiment. Sensor 100 senses the concentration of chemicals in a solution generally, and in a preferred embodiment, senses the concentration of chemicals in a liquid decontaminate (e.g., an aqueous solution of hydrogen peroxide) by use of a capacitor, as will be described in detail below. FIG. 3 provides a detailed schematic of sensor 100 according to the first embodiment. In this embodiment, sensor 100 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the concentration of chemicals in a liquid decontaminate (e.g., an aqueous solution of hydrogen peroxide). Sensor 100 is generally comprised of a voltage source 122 that acts as a signal generator, a null detector 130, an electronic potentiometer 140, a capacitor 108 of known capacitance $C_1$, and a capacitor 110 of capacitance $C_x$. Sensor 100 is electrically connected to system controller 98 to communicate electrical signals therebetween, as will be described below (See FIG. 1).

Capacitor 110 acts as a sensing element, and is directly exposed to the liquid decontaminate in feed line 54 as shown in FIG. 1. In one embodiment, capacitor 110 is a parallel plate capacitor. However, it should be appreciated that capacitor 110 could be constructed in a different form. For example, capacitor 110 could be a cylindrical or spherical capacitor. If a spherical capacitor is used as capacitor 110, holes must be placed in the outer shell of the capacitor such that liquid decontaminate can enter and exit the capacitor.

As stated above, in a preferred embodiment of the present invention, the liquid decontaminate is an aqueous solution of hydrogen peroxide. Therefore, in a preferred embodiment, capacitor 110 is directly exposed to an aqueous solution of hydrogen peroxide. Capacitor 110 is preferably disposed within feed line 54 in such a way that the liquid decontaminate in feed line 54 fills the gap between the conducting plates of capacitor 110, thereby acting as the insulator or "dielectric" of capacitor 110. Sensor 100 provides data indicative of a capacitance $C_x$, corresponding to a chemical concentration. In this regard, capacitance $C_x$ will vary in accordance with the concentration of chemical components in the liquid decontaminate.

It should be appreciated that capacitor 110 may be alternatively disposed in such a way as to sense chemical concentrations within liquid decontaminate supply 52, or at any location within vaporizer 30 where liquid decontaminate may be present.

Referring now to FIG. 2, electronic potentiometer 140 functions in the same manner as a mechanical potentiometer. In this regard, electronic potentiometer 140 is a three terminal device. Between two of the terminals is a resistive element. The third terminal, known as the "wiper," is connected to various points along the resistive element. In a preferred embodiment, the wiper is digitally controlled by system controller 98 (see FIG. 1). It is appreciated that the wiper could be controlled by a controller other than controller 98. The wiper divides the resistive element into two resistors $R_{BC}$ and $R_{AC}$. Electronic potentiometer 140 may take the form of a digitally programmable potentiometer (DPP™) available from Catalyst Semiconductor, Inc. of Sunnyvale, Calif.

Voltage source 122 provides an AC voltage signal, such as a sinusoidal or pulse waveform. Null detector 130 is a device for detecting a null condition (i.e., a short circuit), such as a galvanometer, a voltmeter, a frequency-selective amplifier, and the like.

Operation of sensor 100, as shown in FIG. 3, will now be described in detail. The elements of the bridge circuit are connected between junctions AC, BC, AD, and BD. Electronic potentiometer 140 is operated by system controller 98 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

Capacitor 110, having capacitance $C_x$, is connected between junctions A and D, and capacitor 108, having capacitance $C_1$, is connected between junctions B and D. Electronic potentiometer 140, connected from junction A to junction C to junction B, is adjusted by system controller 98 to vary the voltages $V_{AC}$ and $V_{BC}$.

When a null is detected by null detector 130, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1 R_{AC} \text{ and } V_{BC}=I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x}$$

-continued $$V_{BD} = \frac{I_2}{2\pi f C_1}$$

As discussed above, $V_{AD}=V_{BD}/(V_{AC}/V_{BC})$, $V_{AC}=I_1 R_{AC}$ and $V_{BC}=I_2 R_{BC}$. Therefore, $$C_x = C_1 \left( \frac{R_{BC}}{R_{AC}} \right).$$

In view of the foregoing relationship, when a null condition is detected, the resistance values for $R_{BC}$ and $R_{AC}$, along with the known capacitance value $C_1$, of capacitor 108, can be used to determine unknown value of capacitance $C_x$ of capacitor 110.

Sensor 100 utilizes differences in dipole moments of different molecules to determine the concentration of a chemical in a liquid decontaminate. As discussed above and shown in FIG. 1 liquid decontaminate traveling through feed line 54 fills the gap between the conducting plates of capacitor 110, thereby acting as the dielectric of capacitor 110. By configuring capacitor 110 as an element of a bridge circuit, a measure of resistance values $R_{AC}$ and $R_{BC}$, when the bridge is balanced or nulled, can be used to determine capacitance $C_x$ of capacitor 110. Capacitance $C_x$ is indicative of the concentrations of the chemical components in the liquid decontaminate, since the permittivity of the respective dielectric is affected by the concentrations of the chemical components of the liquid decontaminate.

Figure 4:
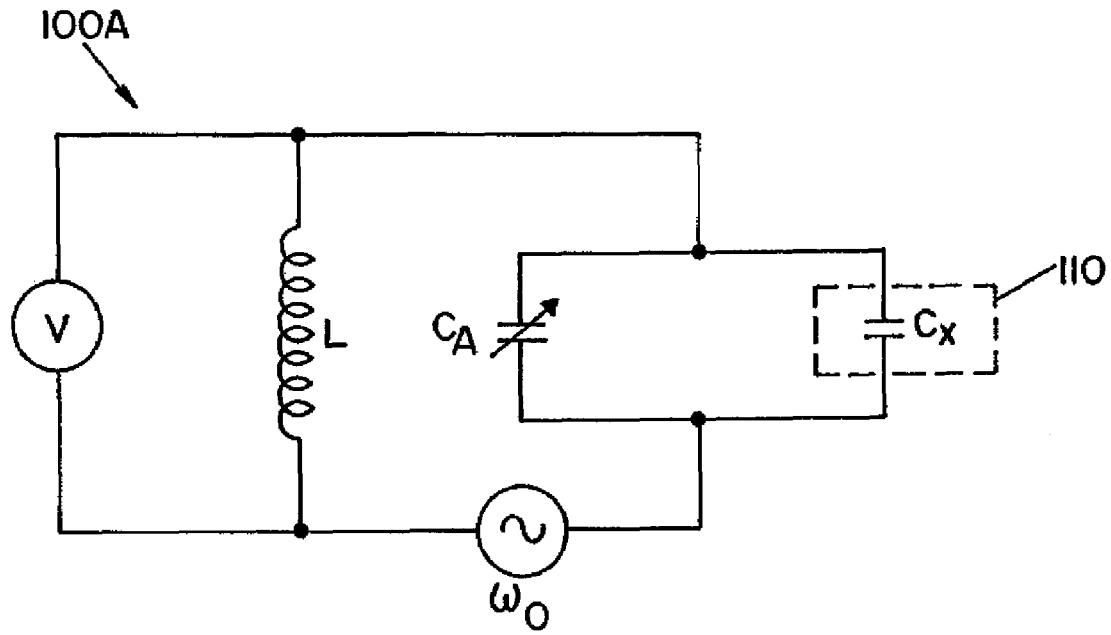
FIG. 4 is a schematic diagram of an exemplary sensor for determining the concentration of a liquid chemical, according to a second embodiment.

It should be appreciated that while the illustrated embodiment of sensor 100 takes the form of a bridge circuit, other types of circuits and techniques (including other types of bridge circuits, and capacitance meters) known to those skilled in the art, may be suitably used to measure capacitance. For example, FIG. 4 illustrates an alternative sensor 100A. Sensor 100A is an LC resonant circuit, having a variable capacitor $C_A$ and a capacitor 110 having a capacitance $C_x$ directly exposed to the liquid decontaminate in feed line 54. In this regard, the liquid decontaminate fills the gap between the conducting plates of capacitor 110, thereby acting as the insulator or "dielectric" of capacitor 110. Since the resonance frequency $\omega_0=[L(C_A+C_x)]^{-1/2}$, the unknown capacitance of capacitor 110 can be determined.

Figure 5:
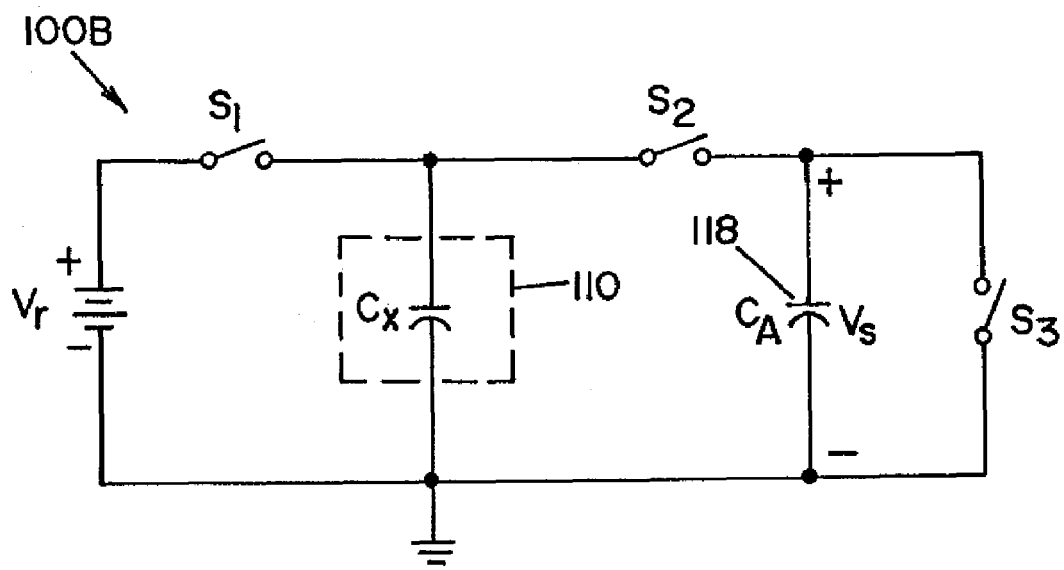
FIG. 5 is a schematic diagram of an exemplary sensor for determining the concentration of a liquid chemical, according to a third embodiment.

FIG. 5 illustrates yet another alternative liquid concentration sensor 100B suitable for use in connection with the present invention. In this embodiment, liquid concentration sensor 100B is a "charge transfer" sensor circuit. Charge transfer sensor circuits are recognized to provide resolutions of fractions of a femtoFarad. In a charge transfer sensor circuit the unknown capacitance $C_x$ of capacitor 110 is determined by charging the sense electrode to a fixed potential, and then transferring that charge to a charge detector comprising a capacitor 118 of known capacitance $C_A$. Liquid decontaminate fills the gap between the conducting plates of capacitor 110 of liquid concentration sensor 100B, thereby acting as an insulator or "dielectric" of capacitor 110. Capacitor 110 is first connected to a DC reference voltage ($V_r$) via a switch $S_1$. Switch $S_1$ is reopened after capacitor 110 is satisfactorily charged to the potential of $V_r$. Then, after as brief as possible a delay so as to minimize leakage effects caused by conductance, switch $S_2$ is closed and the charge (Q) present on capacitor 110 is transferred to capacitor 118 (i.e., the charge detector). Once the charge Q is satisfactorily transferred to capacitor 118, switch $S_2$ is reopened. By reading voltage $V_s$, the capacitance $C_x$ of capacitor 110 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 118 is selected to have significantly more capacitance than capacitor 110.

The equations governing this alternative embodiment are as follows:

$$V_s = V_r[C_x/(C_x+C_A)], \text{ therefore}$$

$$C_x = V_s C_A/[V_r - V_s].$$

It is recognized that in some cases, the capacitance of the capacitor exposed to the liquid decontaminate located in feed line 54 may be in the range of femtoFarad capacitance to low picoFarad capacitance (e.g., 1 fF to 100 pF), and that changes in concentration of a chemical in the liquid decontaminate may only result in a change of capacitance in the range of low picoFarad capacitance or even femtoFarad capacitances. Accordingly, the sensor circuit used to measure capacitance may need to have high sensitivity to allow for measurement of small values of capacitance. One high sensitivity sensor circuit is the charge transfer sensor circuit described above. Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10-7 pF to 10 μF. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

With reference to FIGS. 1-3, operation of sensor 100, according to a preferred embodiment, will now be described in detail. As a preliminary step, system controller 98 stores in memory 96 a set of data comprising values of the capacitance of capacitor 110 having a capacitance $C_x$ for a plurality of concentrations of a liquid decontaminate. This set of data may be determined by exposing capacitor 110 of sensor 100 to several different combinations of concentrations of a decontaminating chemical in the liquid decontaminate, and recording the corresponding measured capacitance $C_x$. For example, system controller 98 may store values of the capacitance $C_x$ of capacitor 110 that are determined for a plurality of concentrations of a liquid decontaminate comprised of only two components. As the concentrations of the first and second components are varied, the corresponding capacitance of capacitor 110 is determined and stored in memory 96. For instance, capacitance of capacitor 110 may be determined for various concentrations of a first component and a second component (at a fixed volume of the liquid decontaminate), including, but not limited to:

0% first component and 100% second component,
25% first component and 75% second component,
50% first component and 50% second component,
75% first component and 25% second component, and
100% first component and 0% second component.

After the set of data is stored in memory 96, measurement of concentrations of a decontaminating chemical in a liquid decontaminate can commence. Capacitor 110 is exposed to a liquid decontaminate in feed line 54. As indicated above, capacitor 110 may be located in liquid decontaminate supply 52, any location within vaporizer 30 where liquid decontaminate may be present, or any other location where capacitor 110 will be exposed to liquid decontaminate. A determination of $R_{AC}$ and $R_{BC}$ when the bridge is nulled is then used to determine a value for the capacitance of capacitor 110. As discussed above, $C_x = C_1(R_{BC}/R_{AC})$. The data stored in memory 96 is searched for the capacitance $C_x$ of capacitor 110 to obtain the corresponding concentrations. A linear relationship between concentration and capacitance allows one to normalize any measurement made so as to provide the concentration of each component in the solution. If the capacitance $C_x$ of capacitor 110 is not found in the pre-stored data, the stored data may be interpolated or extrapolated to obtain a concentration corresponding to the measure capacitance of capacitor 110. As noted above, frequency of the waveform generated by voltage source 122 will influence the response of capacitors. Where the capacitance $C_x$ of capacitor 110 does not exhibit a suitable linear response, an expanded set of data points should be stored in memory 96, so that interpolation or extrapolation is unnecessary.

It should be appreciated that while a preferred embodiment of the present invention uses a measure of a capacitor's capacitance to determine concentrations, it is also contemplated that a measure of other electrical properties of a capacitor may be used to determine concentrations, including, but not limited to, the permittivity and dielectric constant of the capacitor dielectric.

In the illustrated embodiment, vapor concentration sensor 200 is of the type described in U.S. application Ser. No. 10/663,593 filed Sep. 16, 2003, entitled "Sensor for Determining Concentration of Fluid Sterilant," which is fully incorporated herein by reference, and described further below.

Figure 6:
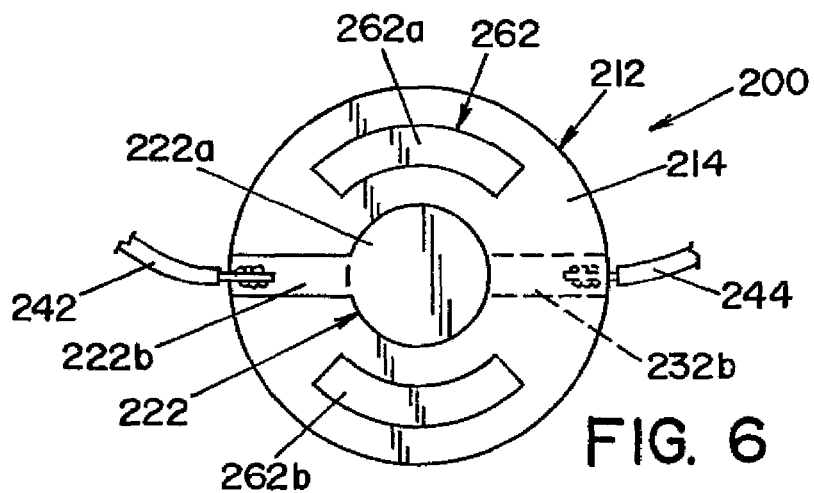
FIG. 6 is a top, plan view of an exemplary sensor for determining the concentration of a gaseous chemical, according to a preferred embodiment.
Figure 7:
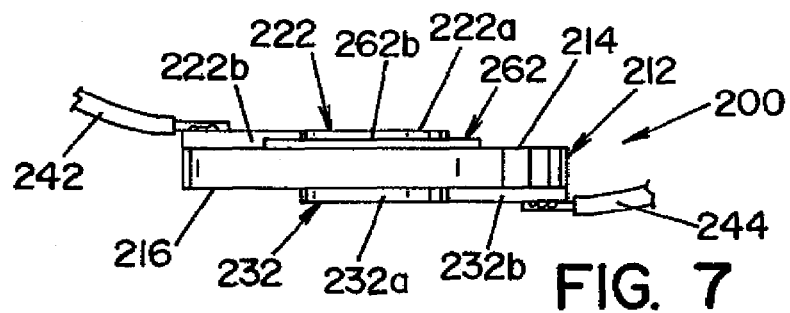
FIG. 7 is a side, elevation view of the sensor shown in FIG. 6.
Figure 8:
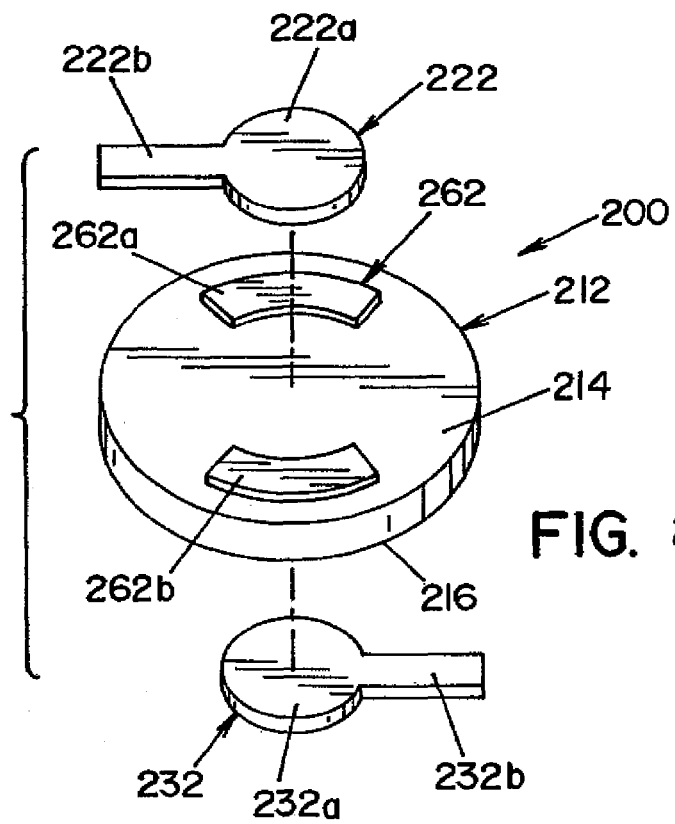
FIG. 8 is an exploded view of the sensor shown in FIG. 6.

Referring now to FIGS. 6-8, vapor concentration sensor 200 is comprised of a sensing element 212 having a layer or coating 262 of a material that interacts with, or is reactive with, the decontaminate used in system 10, such that mechanical motion or movement of sensor 200 is converted into an electrical signal and transmitted to system controller 98.

Element 212 may be a moving or suspended component, but in a preferred embodiment, element 212 is a piezoelectric device, and more preferably, is a quartz crystal. Other piezoelectric materials, such as by way of example and not limitation, Rochelle salt, barium titanate, tourmaline, polyvinylidene fluoride and crystals that lack a center of symmetry are also contemplated. In the embodiment shown, element 212 is a flat, circular quartz disk having a first planar, major surface 214 and a second planar, major surface 216. An electrode 222 is disposed on the first major surface 214 and an electrode 232 is disposed optionally on the second major surface 216.

Electrode 222 includes a main body portion 222a that is centrally disposed on first major surface 214 and a leg portion 222b that extends in a first direction to the edge of element 212. Similarly, electrode 232 includes a main body portion 232a that is centrally disposed on second major planar surface 216, and a leg portion 232b that extends in a direction opposite to the first direction of leg portion 222b, wherein leg portion 232b extends to the edge of element 212. Main body portions 222a, 232a of electrodes 222, 232 are disposed respectively on first and second major surfaces 214, 216 to be aligned with each other on opposite sides of element 212. Leg portions 222b, 232b extend in opposite directions from central body portions 222a, 232a, as best seen in the drawings. Electrodes 222, 232 are deposited onto first and second planar surfaces 214, 216. Electrodes 222, 232 may be formed of any electrically conductive material, but are preferably formed of copper, silver or gold. Electrical leads 242, 244 are attached to leg portions 222b, 232b of electrodes 222, 232. Leads 242, 244 are soldered, brazed or welded to electrodes 222, 232 to be in electrical contact therewith.

At least one of the two major surfaces 214, 216 of element 212 is coated with a layer 262 of a material that interacts, or is reactive with, the decontaminate to be used within system 10. In the embodiment shown, layer 262 is on major surface 214. In the embodiment shown, layer 262 is defined by two arcuate or crescent-shaped layer areas 262a, 262b of material applied to first major surface 214 of element 212. Arcuate layer areas 262a, 262b are disposed on first major surface 214 such that electrode 222 is disposed therebetween. The material forming layer areas 262a, 262b are preferably fixedly attached to surface 214 of element 212. The mass of the material on element 212 is dependent upon the desired performance characteristics of vapor concentration sensor 200. As indicated above, the material forming layer areas 262a, 262b is preferably one that interacts or reacts with the decontaminate used within system 10.

In the illustrated embodiment, the decontaminate to be detected by vapor concentration sensor 200 is vaporized hydrogen peroxide, and the material that forms layer areas 262a, 262b on first major surface 214 of vapor concentration sensor 200 is a metal oxide, namely, lead dioxide ($PbO_2$). It is believed that other metal oxides having various states, such as silver (II) oxide (AgO) or manganese (IV) oxide ($MnO_2$), may be used. It is also contemplated that metal oxides having mixed valency states, such as by way of example and not limitation, a metal oxide having a mixture of single and divalent oxide states may be used.

In the illustrated embodiment, sensor 200 is disposed within supply conduit 42 and is connected to system controller 98 as shown in FIG. 1, to provide electrical signals thereto. It should be understood that sensor 200 may be alternatively disposed in such a way as to sense the concentration of vaporized hydrogen peroxide within treatment chamber 24 or within vaporizer 30.

System controller 98 includes an oscillating circuit (not shown) that is connected to sensor 200 to convert movement of sensor 200 into electrical signals, as is conventionally known. System controller 98 also includes stored data indicative of the electrical responses of sensor 200 to predetermined concentrations of a decontaminate to be sensed. In the embodiment heretofore described, where sensor 200 is a quartz crystal and layer areas 262a, 262b are lead dioxide, the data relating to sensor 200 that is stored within system controller 98 is empirical data accumulated under controlled, laboratory conditions.

The empirical data relating to sensor 200 that is stored in system controller 98 may be acquired as follows. The natural frequency of a quartz crystal (without a coating thereon) is measured. The lead dioxide is applied to the quartz crystal and the mass of the coating is determined using the Sauerbre equation. The quartz crystal is then exposed to various, controlled concentrations of vaporized hydrogen peroxide. A graph of the change in frequency per unit mass of coating (or, using the Sauerbre equation, the change in weight per unit mass of coating) versus concentration of decontaminate or oxidant is produced and stored in a data storage device within system controller 98. Alternatively, the data could be stored not as a graph but rather in look-up tables. As will be appreciated, if a coating of uniform thickness is applied to a crystal, the change in frequency or weight could be normalized on a per unit surface area basis.

As suggested, in one embodiment, the change in frequency or weight is divided by the mass of the coating applied to the quartz crystal so that regardless of the mass of coatings applied to other crystals, the change in frequency will be normalized to a unit mass of the coating. Data taken with other quartz crystals that may have coatings of different amounts of mass than the laboratory crystal can still be compared to the stored data obtained from the laboratory crystal as both sets of data will be normalized to a change in frequency or weight per unit mass of the coating. It will be appreciated that with modern deposition means, it may not be necessary to normalize the data as coatings with little physical variation can be deposited from one crystal to the next.

In another embodiment, a quartz crystal is coated with lead oxide and is then exposed to known concentrations of vaporized hydrogen peroxide so as to develop a set of data, or a curve, of equilibrium frequency reduction values as a function of concentration of vaporized hydrogen peroxide for the quartz crystal. The coated quartz crystal is then installed in system 10. The associated set of data, or curve, is programmed or stored in memory 96 of system controller 98. Thus, the data stored in system controller 98 matches the crystal sensor within vapor concentration sensor 200, thereby providing a standardized system. In this manner, vapor concentration sensor 200 has a coated quartz crystal sensor with an associated standardized data set stored within memory 96, as the stored data set was produced by exposing that specific quartz crystal to known concentrations of vaporized hydrogen peroxide.

Vapor concentration sensor 200 operates based upon the concept that the frequency of a piezoelectric device will change in relation to a change in mass of a layer on the device, as a result of exposure to vaporized hydrogen peroxide.

Specifically, the frequency of a piezoelectric device is related to the mass change, as determined by the Sauerbre equation:

$$\Delta f = -(C_f)(\Delta m)$$

$$\Delta f = -(f_o^2/N\rho)\Delta m$$

where:
$\Delta f$ is the frequency change
$\Delta m$ is the mass change per unit area on the surface of the piezoelectric device
$C_f$ is a sensitivity constant
$f_o$ is the operating frequency of the piezoelectric device prior to the mass change
N is the frequency constant for the piezoelectric device
$\rho$ is the density of the piezoelectric device It should be appreciated that sensor 200 may be disposed within system 10 in such a way that best senses the surrounding vapor. Various methods for installing sensors in flowing fluids will be recognized by one skilled in the art. By way of example and not limitation, these include screens, changes in conduit diameter, stilling wells and other methods to expose a sensor to a fluid such as a liquid decontaminate or a vapor for the appropriate amount of time with the appropriate amount of contact.

It should be understood that liquid concentration sensor 100 and vapor concentration sensor 200 as described in connection with the illustrated embodiment of the present invention are only exemplary sensors, and are not intended to limit the scope of the present invention. In this regard, it is contemplated that sensors 100 and 200 may be selected from any suitable sensors known to one skilled in the art. For instance, sensor 200, as described above, may also be suitable for use in detecting concentrations in a liquid, and thus may be substituted for sensor 100. Furthermore, vapor concentration sensor 200 could be of the type described in U.S. application Ser. No. 10/405,880, filed Apr. 2, 2003, entitled "Method and Apparatus for Measuring Concentration of a Chemical Component in a Gas Mixture," which is fully incorporated herein by reference. Furthermore, sensors 100, 100A and 100B, as described above, may also be suitable for use in detecting concentrations in a vapor, and thus may be substituted for sensor 200.

The present invention shall now be further described with reference to the operation of system 10. In a preferred embodiment, pump 62 dispenses an aqueous solution of hydrogen peroxide into vaporizer 30 where the aqueous solution of hydrogen peroxide is vaporized. The vaporized hydrogen peroxide and vaporized water pass through supply conduit 42 into treatment chamber 24 where articles to be sterilized or decontaminated are disposed. Vaporized hydrogen peroxide is supplied to treatment chamber 24 in amounts sufficient to effect decontamination of the articles disposed therein.

Over time, the effectiveness of a decontamination cycle as described by the foregoing may decrease due to a reduced vaporization efficiency of vaporizer 30. The reduction in vaporization efficiency of vaporizer 30 may occur when evaporation surfaces such as those of heating element 32 within vaporizer 30 develop contamination or scale buildup that reduces the efficiency of heat transfer. As the heat transferred is reduced, the rate of vaporization also decreases. The rate of vaporization should be substantially instantaneous for a vaporizer 30 to function correctly. If vaporization is not substantially instantaneous, puddles of unevaporated aqueous solution of hydrogen peroxide may accumulate within the vaporizer. When such puddles accumulate, vaporization becomes dependent upon the relative partial pressures of the components of the decontaminate.

By way of example and not limitation, in the embodiment shown, the aqueous solution of hydrogen peroxide supplied to vaporizer 30 is typically comprised of about 65% water and about 35% hydrogen peroxide (by weight). If such a solution were substantially instantaneously vaporized, the proportions of hydrogen peroxide and water in the vapor would also be about 65% water and about 35% hydrogen peroxide. However, if such a solution were not substantially instantaneously vaporized, preferential boiling due to the differing vapor pressures of water and hydrogen peroxide would result in a vapor concentration of water in excess of 65%. The concentration of hydrogen peroxide in the vapor from vaporizer 30 would therefore be less than 35%.

Vaporization efficiency can function as a metric to be used for the identification of vaporization problems that may affect sterilization. For example, a decrease of the vaporization efficiency over time indicates that the concentration of hydrogen peroxide in the vapor leaving vaporizer 30 is less than the concentration of the hydrogen peroxide in the aqueous solution entering vaporizer 30 from feed line 54. In such a situation, an operator could be notified that vaporizer 30 is in need of cleaning.

An advantage of using vaporization efficiency as a metric is that it can provide automatic monitoring of the operation of vaporizer 30 without the need for direct physical inspection of vaporizer 30. Another advantage is that fluctuations of the concentration of vaporized hydrogen peroxide that are a result of fluctuations of the concentration of hydrogen peroxide in the aqueous solution of hydrogen peroxide in feed line 54 may be compensated for by appropriate timing of data acquisition, as will be discussed further below.

As used herein, an "efficiency of vaporization" is used to express the concentrations of hydrogen peroxide in a liquid solution and in a vapor resulting from that solution. In the embodiment shown, the efficiency of vaporization of vaporizer 30 is monitored by system controller 98. It is appreciated that the efficiency of vaporization may be monitored continuously or periodically during a given cycle or a given phase of a cycle (e.g., the decontamination phase), as necessary, to ensure that vaporizer 30 is in proper working order.

In order to describe the efficiency of vaporization as used to monitor and describe the condition of vaporizer 30 and the effectiveness of system 10, it is necessary to define terms that will be used to further describe the method for determining the vaporization efficiency of a sterilizer.

As used herein, the term "actual vaporization efficiency" refers to the concentration of hydrogen peroxide in the vapor divided by the concentration of hydrogen peroxide in the aqueous solution being supplied to vaporizer 30.

As used herein, the term "baseline vaporization efficiency" refers to an "actual vaporization efficiency" determined at some point in time for later use as a benchmark to determine the performance of the vaporizer.

As used herein, the term "effective vaporization efficiency" refers to the ratio of "actual vaporization efficiency" to "baseline vaporization efficiency." The effective vaporization efficiency may be used to evaluate the performance of various systems 10 or of a given system 10 with different vaporizers 30.

In a preferred embodiment, given perfect conditions and assuming no decomposition of hydrogen peroxide prior to vapor concentration sensor 200, the actual vaporization efficiency would be 100%. The actual vaporization efficiency is determined by dividing the concentration of hydrogen peroxide in the vapor produced by vaporizer 30 (e.g., 35%) by the concentration of hydrogen peroxide of the aqueous solution of hydrogen peroxide provided to vaporizer 30 (e.g., 35%).

It is contemplated that on initial startup and qualification of a system 10, the actual vaporization efficiency of vaporizer 30 may not be 100%. Therefore in a preferred embodiment, the baseline vaporization efficiency is determined prior to installation and regular use of system 10. The baseline vaporization efficiency can be used as a basis for comparison with the actual vaporization efficiency to determine whether the rate of heat transfer and therefore scale buildup within vaporizer 30 has changed such that maintenance of vaporizer 30 or replacement of vaporizer 30 is required.

It is further contemplated that baseline vaporization efficiency may be directly compared with an actual vaporization efficiency in order to determine the decontamination effectiveness of system 10. Such a comparison would be effective when sensor 200 is disposed in a location or a manner such that the hydrogen peroxide concentration in the vapor is not affected by factors other than vaporization efficiency.

A mathematical method for comparing the baseline vaporization efficiency with the actual vaporization efficiency is the calculation of effective vaporization efficiency. Effective vaporization efficiency is determined by dividing the actual vaporization efficiency by baseline vaporization efficiency. During operation of system 10, the effective vaporization efficiency may be monitored by system controller 98 to determine the current effectiveness of vaporizer 30 within system 10. Vaporizer 30 can be refurbished, cleaned, or otherwise brought into acceptable condition when the effective vaporization efficiency drops below the desired level. The minimum desired level of effective vaporization efficiency is determined prior to operation of system 10.

A method of determining the efficiency in a decontamination system will now be described in accordance with a preferred embodiment of the present invention, as shown in FIG. 1. As illustrated in FIG. 1, sensing element 110 is disposed within feed line 54 and vapor concentration sensor 200 is disposed within supply conduit 42.

Figure 9:
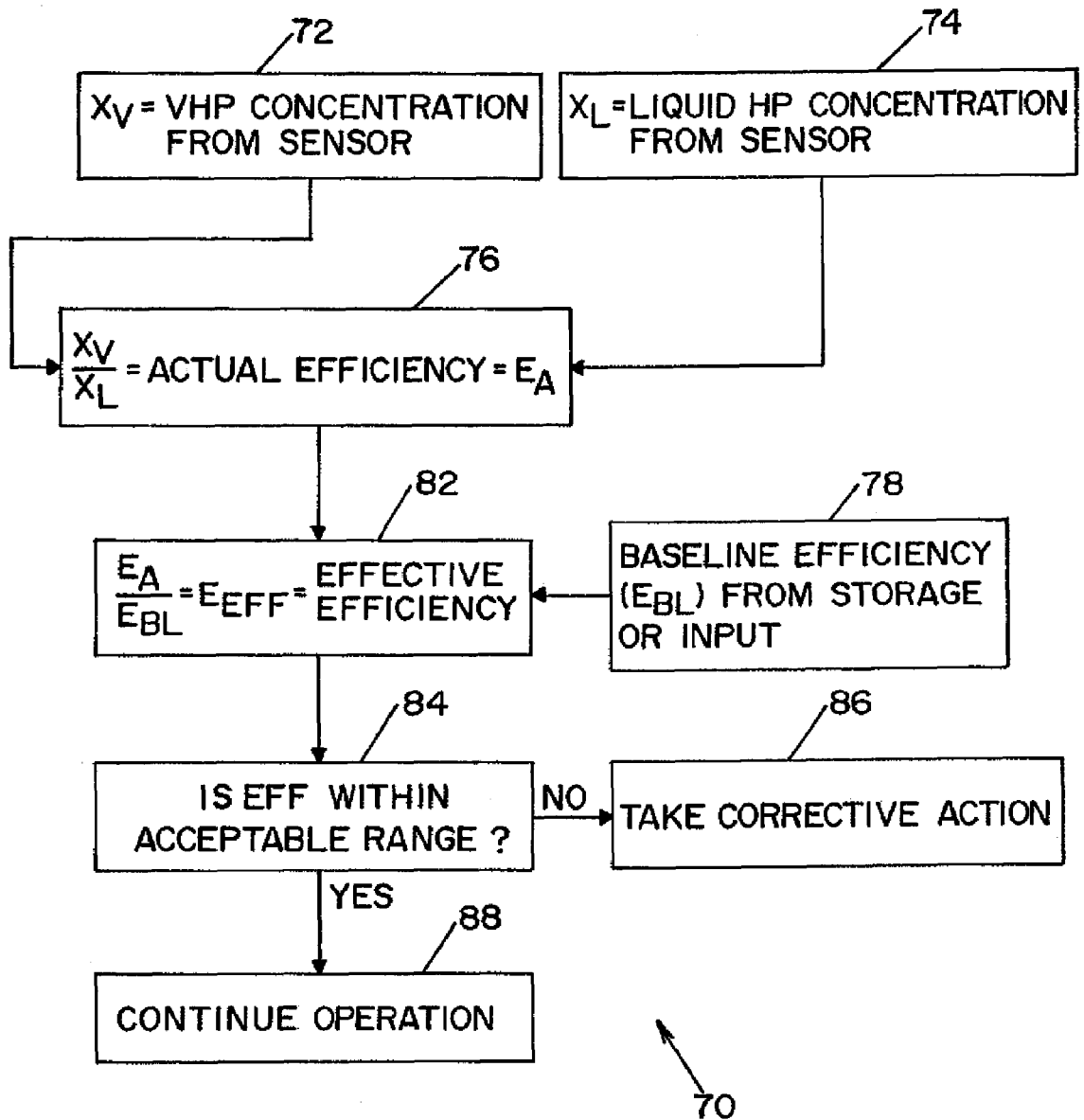
FIG. 9 is a flow chart of a method for determining the efficiency of vaporization for hydrogen peroxide, according to a preferred embodiment of the present invention.

Referring now to FIG. 9, there is shown a method 70 for determining vaporization efficiency for vaporizer 30. Liquid concentration sensor 100 provides data indicative of the hydrogen peroxide concentration $X_L$ to system controller 98 in step 74. Similarly, vapor concentration sensor 200 provides data indicative of the concentration of vaporized hydrogen peroxide, $X_V$, to system controller 98 in step 72.

It is appreciated that $X_L$ and $X_V$ represent concentrations of hydrogen peroxide in the liquid decontaminate and the vapor mixture to be sampled at a given moment in time and at a given place, and may fluctuate for various reasons other than the operation of vaporizer 30. Therefore, it may be desirable to calculate the actual vaporization efficiency $E_A$ using values of $X_L$ and $X_V$ that generally represent the concentrations of a particular unit mass of the decontaminate to be sampled in both the liquid decontaminate and the vapor mixture. In this way variations of BA due to reasons other than the operation of the vaporizer 30 would be reduced. Thus, fluctuations of $E_A$ would be more attributable to the operation of vaporizer 30.

System controller 98 determines the actual vaporization efficiency $E_A$ using values $X_V$ and $X_L$. As shown in step 76 of FIG. 9;

$$\frac{X_v}{X_L} = E_A$$

In step 82, actual vaporization efficiency $E_A$ is compared to base line efficiency $E_{BL}$ obtained from storage or input (step 78), and an effective vaporization efficiency $E_{EFF}$ is calculated.

$$E_{EFF} = \frac{E_A}{E_{BL}}$$

The baseline vaporization efficiency of $E_{BL}$ may be entered and/or stored in system controller 98 as a single value or may be part of a data table stored within system controller 98. The effective minimum efficiency may also be entered and/or stored in controller 98.

In step 84, the effective vaporization efficiency $E_{EFF}$ is compared to predetermined threshold values/ranges to determine whether $E_{EFF}$ is within an acceptable range. The predetermined values may be stored in system controller 98. Step 84 may take place electronically within system controller 98 or step 84 may be conducted manually.

If the effective vaporization efficiency $E_{EFF}$ is within an acceptable range, the operation of decontamination continues as normal, as shown in step 88. If the effective vaporization efficiency is not within the acceptable range, the operator may be alerted to the condition by audible or visible indicators. The operator may then take corrective action as shown in step 86 in FIG. 9 that may include extension of the current decontamination cycle in order to effectively sterilize or insure an effective decontamination of the device as disposed within system 10. Alternatively, the decontamination cycle may be stopped immediately and vaporizer 30 may be replaced or maintained in a manner such that it can vaporize with an acceptable effective vaporization efficiency $E_{EFF}$. As another alternative, the decontamination cycle may be continued to the end and maintenance performed on vaporizer 30 at the completion thereof. If necessary, vaporizer 30 may be replaced as necessary.

The present invention shall now be further described with respect to various hypothetical vaporization efficiencies are determined for various given concentrations of hydrogen peroxide.

EXAMPLE

| HYPOTHETICAL VAPORIZATION EFFICIENCIES TABLE | | |
|---|---|---|
| $X_L$ (conc. of liquid hydrogen peroxide) | 34% | 34% |
| $X_V$ (conc. of vaporized hydrogen peroxide) | 34% | 30% |
| $E_A(calc) = \dfrac{X_V}{X_L}$ | 1.00 | 0.88 |
| $E_{BL}$ | 1.00 | 1.00 |
| $E_{EFF}(calc) = \dfrac{E_A}{E_{BL}}$ | 1.00 | 0.88 |
| Minimum Effective vaporization efficiency | 0.9 | 0.9 |
| Compare $E_{EFF}$ and Min $E_{EFF}$ | 1.00 > 0.9 | 0.88 < 0.9 |

It should be appreciated that while a preferred embodiment of the present invention has been described with reference to determining an efficiency of vaporization for vaporized hydrogen peroxide, it is contemplated that the present invention finds utility in determining an efficiency of vaporization for other chemical components. These chemical components may comprise decontaminating chemicals, including, but not limited to, chemicals selected from the group consisting of: hypochlorites, iodophors, quaternary ammonium chlorides (Quats), acid sanitizers, aldehydes (formaldehyde and glutaraldehyde), alcohols, phenolics, peracetic acid (PAA), and chlorine dioxide.

Specific examples of decontaminating chemicals, include, but are not limited to, hydrogen peroxide, peracids such as peracetic acid, bleach, ammonia, ethylene oxide, fluorine containing chemicals, chlorine containing chemicals, bromine containing chemicals, vaporized hydrogen peroxide, vaporized bleach, vaporized peracid, vaporized peracetic acid, ozone, ethylene oxide, chlorine dioxide, halogen containing compounds, other highly oxidative chemicals (i.e., oxidants), and mixtures thereof.

The decontaminating chemicals may also be combined with other chemicals. Examples of other chemicals that may be combined with decontaminating chemicals, include, but are not limited to, water, de-ionized water, distilled water, an alcohol (e.g., a tertiary alcohol), a glycol-containing chemical compound, and mixtures thereof. Glycol-containing chemical compounds include, but are not limited to, polyethylene glycol, diethylene glycol, triethylene glycol, tetraethylene glycol, glycol ethers, polypropylene glycol, propylene glycol, de-ionized water vapor, distilled water vapor, a vaporized alcohol (e.g., a tertiary alcohol), and mixtures thereof.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having defined the invention, the following is claimed:

1. A method for determining efficiency of a vaporizer for a vaporization process, the method comprising the steps of:
   storing a plurality of first data values in a memory, wherein said first data values are indicative of an electrical property of a capacitor in response to a plurality of predetermined concentrations of hydrogen peroxide in a liquid decontaminate,
   exposing a first sensor, having a capacitor, to the liquid decontaminate including hydrogen peroxide, wherein the electrical property of the capacitor is used to generate a first signal indicative of the concentration of hydrogen peroxide in the liquid decontaminate before vaporization by a vaporizer;
   vaporizing the liquid to produce a gas including a vaporized decontaminate; and
   exposing a second sensor to the gas, wherein the second sensor generates a second signal indicative of the concentration of vaporized hydrogen peroxide in the vaporized decontaminate;
   determining concentration of hydrogen peroxide in the liquid decontaminate ($X_L$) using the first signal and said plurality of first data values;
   determining concentration of the vaporied hydrogen peroxide ($X_V$) using the second signal; and
   determining actual vaporization efficiency ($E_A$) according to $E_A = X_V/X_L$.

2. A method as defined in claim 1 further comprising:
   establishing a baseline efficiency ($E_{BL}$), wherein $E_{BL}$ is a predetermined baseline efficiency for evaluating performance of said vaporizer; and
   determining an effective vaporization efficiency ($E_{EFF}$) according to $E_{EFF} = E_A/E_{BL}$.

3. A method as defined in claim 2, wherein said method further comprises:
   comparing the determined effective vaporization efficiency ($E_{EFF}$) to a predetermined value in order to determine whether $E_{EFF}$ is acceptable.

4. A method as defined by claim 3, wherein said method further comprises:
   alerting an operator to an unacceptable condition if $E_{EFF}$ is not acceptable.

5. A method as defined by claim 1, wherein said liquid includes at least one additional chemical component, and said gas includes at least one additional chemical component.

6. A method as defined in claim 1, wherein said first sensor is located in a conduit in fluid communication with a liquid decontaminate supply and said vaporizer.

7. A method as defined in claim 1, wherein said first sensor is located in a liquid decontaminate supply for supplying liquid decontaminate to said vaporizer.

8. A method as defined in claim 1, wherein said second sensor is located in a conduit in fluid communication with said vaporizer and a treatment chamber.

9. A method as defined in claim 1, wherein said second sensor is located in said treatment chamber, said treatment chamber receiving the vaporized decontaminate.

10. A method as defined in claim 1, wherein said second sensor includes a piezoelectric device having a material that interacts or is reactive with vaporized hydrogen peroxide.

11. A method as defined in claim 1, wherein said method further comprises
    storing a plurality of second data values in said memory, wherein said second data values are indicative of electrical responses of the second sensor to a plurality of predetermined concentrations of vaporized hydrogen peroxide.

* * * * *